(12) United States Patent
Ficker et al.

(10) Patent No.: US 11,617,668 B2
(45) Date of Patent: Apr. 4, 2023

(54) BRANCHED STENT AND STENT SYSTEM

(71) Applicant: FREISTAAT BAYERN VERTRETEN DURCH HOCHSCHULE HOF, INSTITUT FÜR MATERIAL WISSENSCHAFTEN, Hof/Saale (DE)

(72) Inventors: Frank Ficker, Tiefenbrunn (DE); Marielies Becker, Berlin (DE)

(73) Assignee: FREISTAAT BAYERN VERTRETEN DURCH HOCHSCHULE HOF, INSTITUT FÜR MATERIAL WISSENSCHAFTEN, Hof/Saale (DE)

( * ) Notice: Subject to any disclaimer, the term of this patent is extended or adjusted under 35 U.S.C. 154(b) by 0 days.

(21) Appl. No.: 17/046,079

(22) PCT Filed: Apr. 11, 2019

(86) PCT No.: PCT/EP2019/059322
§ 371 (c)(1),
(2) Date: Oct. 8, 2020

(87) PCT Pub. No.: WO2019/197565
PCT Pub. Date: Oct. 17, 2019

(65) Prior Publication Data
US 2021/0030569 A1 Feb. 4, 2021

(30) Foreign Application Priority Data
Apr. 11, 2018 (DE) .................. 10 2018 108 584.2

(51) Int. Cl.
*A61F 2/856* (2013.01)
*A61F 2/86* (2013.01)

(52) U.S. Cl.
CPC ............. *A61F 2/856* (2013.01); *A61F 2/86* (2013.01); *A61F 2210/0014* (2013.01)

(58) Field of Classification Search
None
See application file for complete search history.

(56) References Cited

U.S. PATENT DOCUMENTS 5,571,135 A * 11/1996 Fraser ................. A61F 2/95
606/198
2003/0097169 A1 * 5/2003 Brucker ............. A61F 2/9662
623/1.11

(Continued)

FOREIGN PATENT DOCUMENTS

DE    10 2012 111 225 A1    5/2014
EP     2 698 130 A1          2/2014

(Continued)

OTHER PUBLICATIONS

PCT Search Report, dated Aug. 7, 2019.
German Patent Office Search Report, dated Oct. 30, 2018.

*Primary Examiner* — Leslie Lopez
(74) *Attorney, Agent, or Firm* — Dority & Manning, P.A.

(57) ABSTRACT

A branched stent includes a main branch having a tubular main lumen and a side branch that branches off from the main branch. The main branch and the side branch are made from a strand-shaped starting material. The side branch is configurable between a first state in which the side branch lies within the main lumen and a second state in which the side lies outside the main lumen. In the second state, the side branch defines a tubular side branch fluidically connected to the main lumen. The side branch is formed at least in part of a shape-memory material.

15 Claims, 8 Drawing Sheets

(56) References Cited

U.S. PATENT DOCUMENTS

| | | | |
|---|---|---|---|
| 2004/0138737 A1* | 7/2004 | Davidson | A61M 25/1002 |
| | | | 623/1.35 |
| 2005/0102023 A1 | 5/2005 | Yadin et al. | |
| 2007/0010874 A1 | 1/2007 | Sun | |
| 2007/0055362 A1* | 3/2007 | Brown | A61F 2/91 |
| | | | 623/1.35 |
| 2008/0161901 A1 | 7/2008 | Heuser et al. | |
| 2009/0264991 A1* | 10/2009 | Paul, Jr. | A61F 2/954 |
| | | | 623/1.35 |

FOREIGN PATENT DOCUMENTS

| | | |
|---|---|---|
| EP | 1 791 498 B1 | 2/2018 |
| WO | WO 2004/026180 A2 | 4/2004 |
| WO | WO 2006/036690 A1 | 4/2006 |
| WO | WO 2016/098113 A1 | 6/2016 |

* cited by examiner

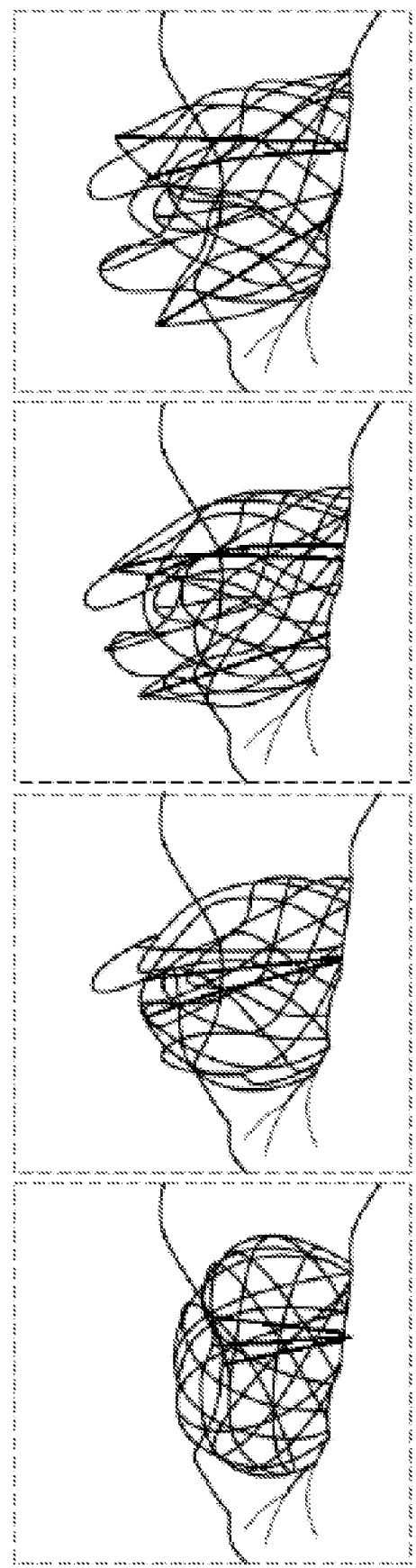

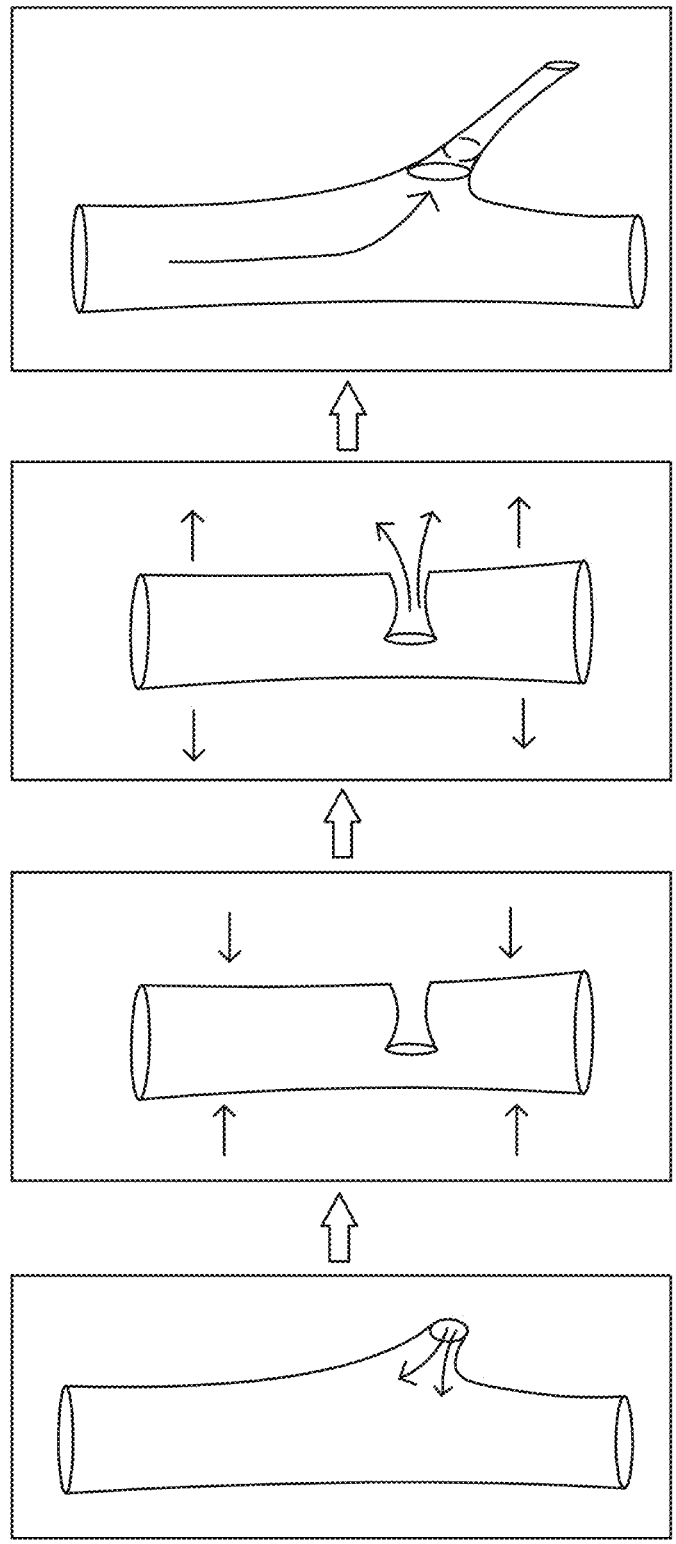

BRANCHED STENT AND STENT SYSTEM

FIELD OF THE INVENTION

The present invention relates to a branched stent made of strand-shaped starting material, in particular of threads and/or wires, comprising a main branch, which includes an essentially tubular main lumen, and a side branch, which branches off from the main branch. The side branch can be transferred from a first state, in which the side branch lies at least partially, preferably completely, inside the main lumen, into a second state, in which the side branch lies outside the main lumen. The side branch in the second state comprises an essentially tubular side branch lumen, which is fluidically connected to the main lumen. Moreover, the invention relates to a stent system comprising a branched stent and a side branch stent.

BACKGROUND

EP 1 791 498 B1 describes a stent graft comprising a tubular body. Stent grafts are utilized in lumina of the human or animal body in order to repair or protect the wall of a vessel of a human or animal patient, for example, in order to span an aneurysm in the vessel. The stent graft comprises at least one opening in the tubular body and a flexible side branch arranged thereon. The tubular body defines a main lumen therethrough, and the flexible side branch is sealingly fastened, as a separate part, around at least one lateral opening of the main branch. Moreover, the flexible, tubular side branch extends into the main lumen and can be turned inside out, in order to extend from the tubular body and provide a tubular side branch in a fluidic connection with the main lumen. In addition, EP 1 791 498 B1 describes a release device for releasing the aforementioned stent graft.

The disadvantage of the stent graft described in EP 1 791 498 B1 is that the complex release device must be utilized for its release. In addition, the flexible side branch has no or only a slight support effect in the region of the opening in the tubular body.

The problem addressed by the present invention is therefore that of providing an improved, branched stent as well as a stent system, which allow for a simpler release and have a greater support effect in the region of the branch-off of a side branch from a main branch of the branched stent.

SUMMARY

The problem is solved with the aid of a branched stent and a stent system having the features set forth herein. Additional objects and advantages of the invention will be set forth in part in the following description, or may be obvious from the description, or may be learned through practice of the invention.

The invention relates to a branched stent made of strand-shaped starting material, in particular of threads and/or wires, comprising a main branch, which includes an essentially tubular main lumen, and a side branch, which branches off from the main branch. Of course, the branched stent can also comprise more than one side branch, wherein the following description also applies similarly for a plurality of side branches.

When threads or wires are described in the following, it is to be noted that other strand-shaped starting materials can also be meant, such as filaments, yarns, or strips.

The side branch can be transferred from a first state into a second state. In the first state, the side branch lies at least partially, preferably completely, inside the main lumen. The first state is therefore utilized for easily bringing the branched stent into the desired position in the lumen of the vessel. Due to the fact that the side branch in the first state lies inside the main lumen, the side branch in no way interferes during the positioning of the branched stent in the lumen. In the second state, the side branch lies outside the main lumen. The side branch has this state when it is arranged in the body in a typical manner. The side branch then extends out of the lumen of the main vessel into the lumen of a branch vessel. The side branch in the second state defines an essentially tubular side branch lumen therethrough, which is fluidically connected to the main lumen. Therefore, an opening, which allows for the fluidic connection to the side branch, is provided in the main branch in addition to the openings at both sides of the tubular main lumen.

According to the invention, the side branch comprises a shape-memory material. The shape-memory material provides two advantages: On the one hand, the shape-memory effect allows for a simpler release of the branched stent. On the other hand, shape-memory materials always have a certain elasticity modulus and, therefore, give stability to the side branch, whereby the side branch and the transitional region receive a support effect.

Advantageously, the shape stored in the shape-memory material of the side branch corresponds to the second state, in which the side branch lies outside the main lumen. The release of the side branch can therefore take place in that the side branch assumes the shape stored in the shape-memory material.

It is advantageous when a holding means is provided, which is operatively connected to the side branch and holds the side branch in the first state. With the aid of the holding means, the side branch is therefore initially held in the first state, so that the branched stent can be easily positioned in the vessel. If the holding means is now released, the side branch assumes the shape stored in the shape-memory material. In particular for the case in which the shape stored in the shape-memory material corresponds to the second state, the transition from the first state into the second state can therefore take place simply by releasing the holding means. As the holding means, for example, threads can be utilized, which are connected at certain points of the side branch and hold the side branch in the first state with the aid of a tensile effect. Other holding means known to a person skilled in the art can also be utilized, however.

It is advantageous when the main branch also comprises a shape-memory material. In the main branch as well, a shape-memory material allows for a simpler release of the branched stent and imparts a certain stability to the main branch. Preferably, the shape-memory material of the main branch is identical to the shape-memory material of the side branch. On the one hand, the physical properties are therefore identical, for example, expansion when heated. On the other hand, and this is more significant, the human or animal body must accept only one shape-memory material. In the case of two different shape-memory materials, the likelihood that at least one of these is rejected by the human or animal body would be considerably greater. In addition, the advantageous manufacture of the stent with the aid of braiding is easier to carry out as a result.

Advantageously, a further holding means is provided, which holds the main branch in a compressed state. Once in a compressed state, the main branch can be easily positioned in the vessel. The further holding means then holds the main branch in the compressed state and, upon release of the holding means, the main branch returns to its original, deployed state.

It is advantageous when the main branch is formed as one piece with the side branch. This allows for an increased stability and support effect of the side branch, in particular in the region of the transition from the main branch to the side branch. Due to the fact that the main branch is formed as one piece with the side branch, for example, the alignment of the side branch with respect to the main branch can therefore also be predefined.

It is advantageous when the branched stent is machined in a textile-like manner. Textile-like machining is understood to mean, for example, braiding, interweaving, knitting, or interknitting. The strand-shaped starting material, i.e., for example, threads as well as wires or any other strand-shaped starting material made of highly diverse materials, can be machined in a textile-like manner. Due to a clever combination of the strand-shaped starting material—for example, with respect to material and thickness—with the textile-like machining technique, the desired properties of the branched stent, in particular compressibility, elasticity, and stability, can be achieved.

Advantageously, the branched stent is braided, in particular on a braider comprising switchable switch-points. A braided branched stent has particularly good properties with respect to elasticity and stability. Due to the braiding on a braider comprising switchable switch-points, the branched stent can also be braided particularly quickly. In the process, for example, the braiding can be started from one end of the main branch. A certain number of threads or wires is braided. At the branch-off of the side branch from the main branch, the threads or wires are now divided into two groups: From one group, the remainder of the main branch is braided up to the other end of the main branch. The side branch is braided from the other group. The side branch is preferably initially braided to be longer than it will finally be. Thereafter, the side branch is shortened to the necessary length.

During the aforementioned division of the threads or wires into two groups, it may happen that a hole forms between the side branch and the main branch. In this case, it is advantageous when crossovers are incorporated by braiding in the region, in which the side branch branches off from the main branch. Therefore, threads or wires that are associated with the side branch or the main branch are crossed over one another. In this way, the hole can be closed. A good and largely consistently tightly braided connection of the side branch onto the main branch is therefore established, whereby a constant support effect can be achieved.

It is advantageous when ends of the starting material, in particular of the wires, from which the branched stent is braided, are connected to loops. Therefore, no exposed wire ends are present, which could result in injury. In addition, threads can be fastened at loops at one end of the side branch as holding means, which hold the side branch in the first state.

Advantageously, the side branch branches off from the main branch at an acute angle. The exact angle depends on the anatomical conditions. In particular when the main branch is formed as one piece with the side branch, the angle corresponding to the anatomical conditions can also be supported. In the case of a branched stent braided from wires made of a shape-memory material, the correct angle is achieved, for example, in that the plaited structure is sintered over a core that has the correct angle.

It is advantageous when the shape-memory material is Nitinol. Nitinol is distinguished by its superelasticity as well as by its good biocompatibility.

It is advantageous when the branched stent comprises a coating, preferably a coating comprising a drug and/or comprising an active substance. These can be drugs that are to prevent a rejection of the branched stent by the human or animal body, as well as drugs that are to deploy a local effect at the position of the branched stent.

In an advantageous embodiment of the stent, the main branch and the side branch have different diameters, wherein the side branch is thinner or thicker than the main branch. Therefore, the anatomy or geometry predefined by the vessel can be addressed in an optimal way and the vessel can be supported in an optimal way. Of course, it can also be advantageous in the individual case when the main branch and the side branch have the same diameter.

If the strand-shaped starting material of the branched stent preferably forms a mesh density varying along the course of the branched stent, a targeted and different support effect or flexibility of the branched stent can be achieved in an advantageous embodiment of the branched stent. The mesh density can vary along (the longitudinal axis of) the branched stent and can also be different in the main branch as compared to the side branch.

Advantageously, the branched stent comprises, at least in some areas, an X-ray-visible material. This X-ray-visible material can indicate the exact position of the main branch and/or the side branch during the implantation under X-ray guidance. The X-ray-visible material is incorporated, in particular, in a textile-like manner, i.e., for example, by braiding in the form of threads, and/or is subsequently applied, for example, as a coating or is introduced into the branched stent as additional material.

If preferably at least a portion of the starting material of the branched stent comprises bioresorbable material, it can dissolve after a certain dwell time in the vessel (of the human or animal body). As a result, a great support effect can be achieved at the beginning and a structure that is as open as possible can be achieved after completion of the healing process.

If, in a preferred embodiment, additional standing threads are introduced into the branched stent in order to stabilize the branched stent, the stability of the branched stent is further increased. The standing threads can have great inherent stability and extend through the branched stent, for example, largely in a straight line, i.e., not in a mesh-forming manner.

Advantageously, the branched stent is surrounded, at least in some areas, by a protective sleeve. The braid is generally open-meshed and merely holds the vessel open and supports it. When the branched stent is surrounded by a protective sleeve, it can additionally seal the vessel.

The branched stent is designed according to the preceding description, wherein the mentioned features can be present individually or in any combination.

Moreover, a stent system comprising a branched stent and a side branch stent is provided. According to the invention, the branched stent is designed according to the preceding description and comprises, in particular, a main branch and a side branch. A side branch designed according to the preceding description is usually relatively short. The side branch therefore operates only, for all intents and purposes, as a door opener for a side branch stent. The diameter of an end of the side branch stent facing the side branch is approximately equal to the diameter of the end of the side branch facing away from the main branch. Therefore, a smooth and well terminating transition from the side branch to the side branch stent is achieved.

BRIEF DESCRIPTION OF THE DRAWINGS

Further advantages of the invention are described in the following exemplary embodiments. Wherein:

FIG. 1b shows a further diagrammatic view of the branched stent from FIG. 1a,

FIG. 2b shows a further end view of the side branch from FIG. 2a, and

FIG. 2c shows a further end view of the side branch from FIG. 2a,

FIGS. 4b through 4e show a stent deployment, and FIGS. 4f through 4i show a "door opener" mode of operation.

DETAILED DESCRIPTION

Figure 1A:
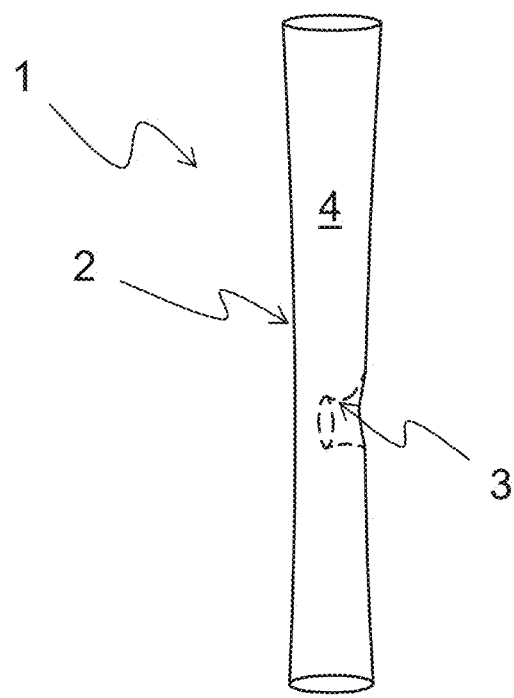
FIG. 1a shows a diagrammatic view of a branched stent.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

In the following description of alternative exemplary embodiments, identical reference numbers are utilized for features that are identical and/or at least comparable. Provided the features are not described in detail again, their design and/or mode of operation correspond/corresponds to the design and mode of operation of the above-described features.

Figure 1B:
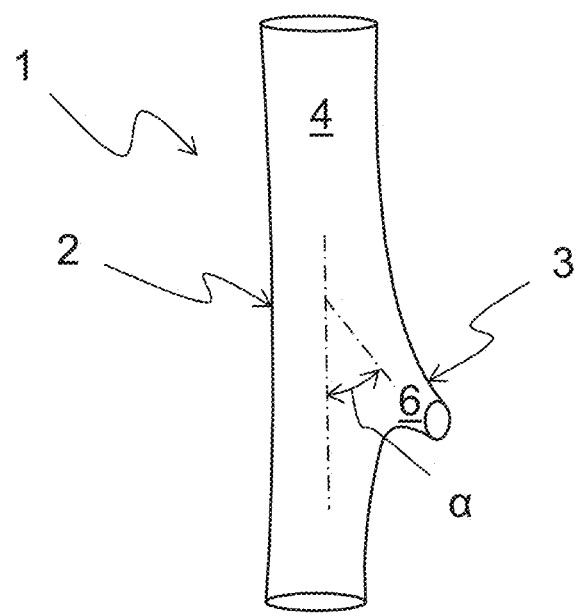

FIG. 1a shows a branched stent 1 comprising a main branch 2 and a side branch 3 (represented using dashed lines). The main branch 2 comprises an essentially tubular main lumen 4. The main branch 2 is made of a shape-memory material, for example, Nitinol, preferably comprising a drug coating, and is held in a slightly compressed state by a further holding means (not shown here), so that it can be easily moved to a position intended therefor. In the compressed state, the main branch 2 can be slightly longer than in its subsequent, second state, in which the side branch 3 lies outside the main lumen 4 (FIG. 1b).

The side branch 3 is formed as one piece with the main branch 2 and, therefore, is also made of the shape-memory material. Preferably, the branched stent 1 is machined in a textile-like manner, in particular with the aid of a braiding technique. In particular, braiding on a braider comprising switchable switch-points has the great advantage that crossovers can be incorporated by braiding, with the aid of which a hole in the gusset of the branch-off between the side branch 3 and the main branch 2, which can arise in the case of a braiding without crossovers, is avoided. A good seal and a largely consistently tightly braided connection of the side branch to the main branch is therefore established.

Figure 2A:
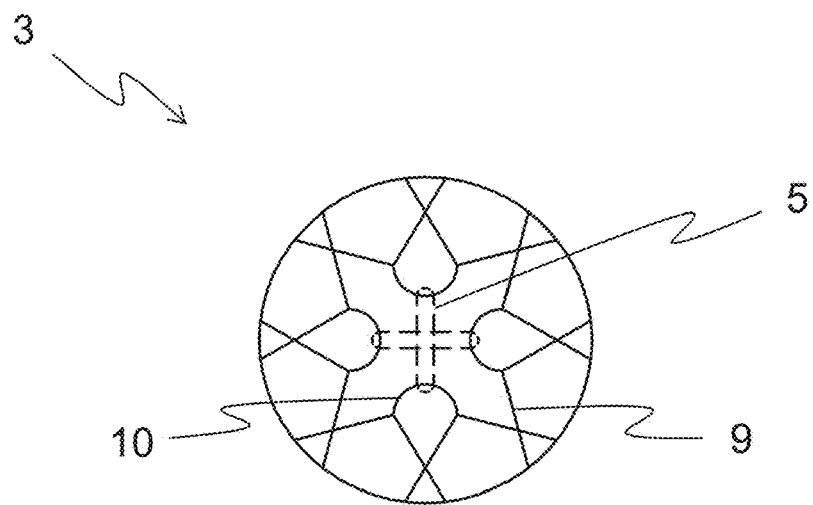
FIG. 2a shows an end view of a side branch.
Figure 2B:
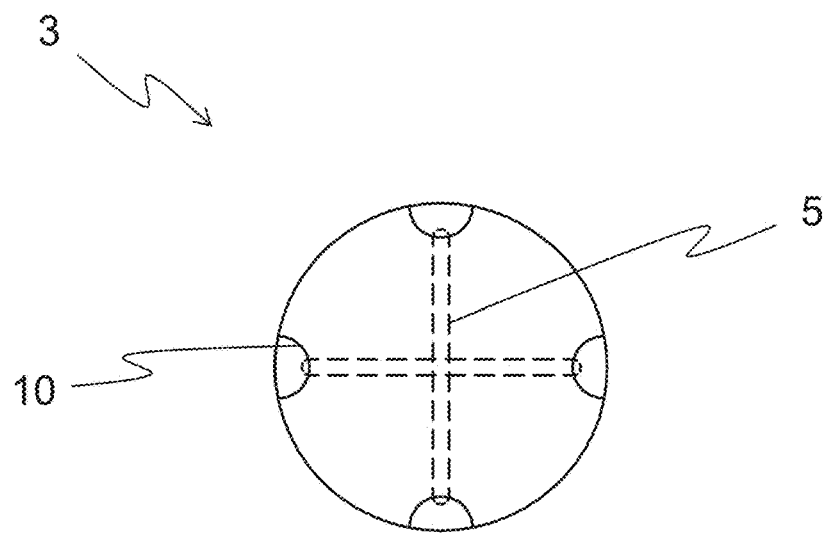

The side branch 3 is held in a first state by a holding means 5 shown, for example, in FIGS. 2a and 2b. In this first state, the side branch 3 is located completely within the main lumen 4, so that it causes no problems during the positioning of the branched stent 1 in a vessel of the human or animal body.

When the branched stent 1 is correctly positioned in the vessel, the holding means 5 and the possible further holding means are released, so that the main branch 2 and the side branch 3 can deploy. The deployment of the side branch 3 transfers the side branch 3 from its first state into its second state, in which the side branch 3 lies outside the main lumen 4.

FIG. 1b shows the branched stent 1 after the deployment. The side branch 3 now defines an essentially tubular side branch lumen 6 therethrough, which is fluidically connected to the main lumen 4. The side branch 3 branches off at an acute angle α from the main branch 2, but is so short that it has no sufficient effect in individual applications in a vessel. Due to the acute angle α, the shape of the stent 1 can be adapted, in an optimal manner, to the branch-off of the main vessel into the lateral vessel in the body. In this case, the side branch 3 can be utilized, for all intents and purposes, as a door opener for a side branch stent 7, which then also has a sufficient supporting function for the vessel.

Figure 1C:
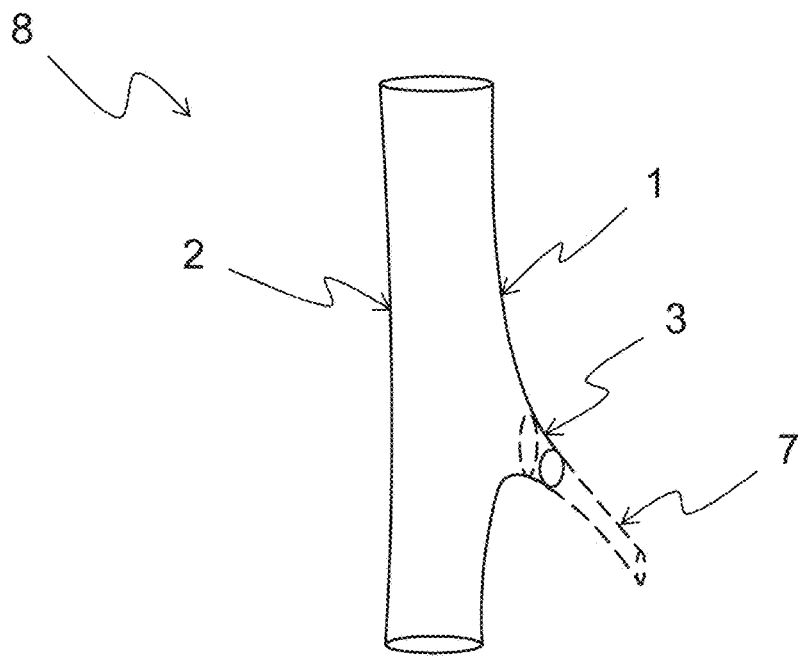
FIG. 1c shows a diagrammatic view of a stent system.

A stent system 8 comprising a branched stent 1 and a side branch stent 7 is shown in FIG. 1c. The side branch stent 7 is represented with the aid of dashed lines for the sake of clarity. In order to position the side branch stent 7 in the lateral vessel, it is guided, in a compressed state, through the main branch 2 and the side branch 3, which is functioning as a door opener in this case. In the deployed state, the side branch stent 7 overlaps with the side branch 3 and, therefore, extends the supporting effect in the lateral vessel. An end of the side branch stent 7 facing the side branch 3 of the stent 1 has approximately the same diameter as the end of the side branch 3 facing away from the main branch 2. Therefore, a smooth and well terminating transition from the side branch 3 to the side branch stent 7 is achieved. Therefore, a risk of injury of the vessel is avoided and the support effect of the vessel can be continuously created.

FIG. 2a shows an end view of a braided side branch 3 in the first state. The ends of the wires 9 of the side branch 3 are connected to loops 10. In this way, no more free ends of wires 9 are present, which represent a risk of injury during the insertion or positioning of the stent into the vessel. Moreover, holding means 5 in the form of threads are bound to the loops 10. These holding means 5 are represented as dashed lines for the sake of clarity. By applying a tensile force through the main lumen 4 of the main branch 2, the holding means 5 pull the loops 10 and, therefore, the end of the side branch 3, together in the manner of a bud.

If the holding means 5 are slightly loosened, the end of the side branch 3 deploys. This is represented in FIG. 2b. The side branch 3 then preferably reassumes its shape stored in the shape-memory material and can deploy into the lateral vessel.

Figure 2C:
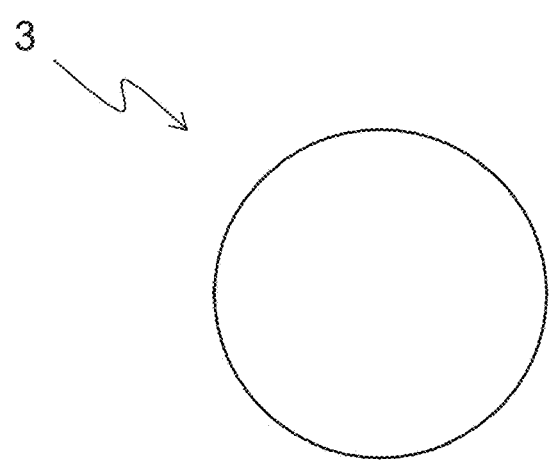

In FIG. 2c, the holding means 5 were finally completely removed, so that the side branch 3 could completely deploy into the second state. The holding means 5 can be removed from the vessel, for example, via the main branch 2.

While the stents 1 were diagrammatically shown in the preceding representations without the representation of meshes, meshes of the stents 1 are indicated in the following figures with the aid of a net-like crosshatching. These are to symbolize the textile-like machining technique, in particular the braiding, in the manufacture of the stent 1.

Figure 3A:
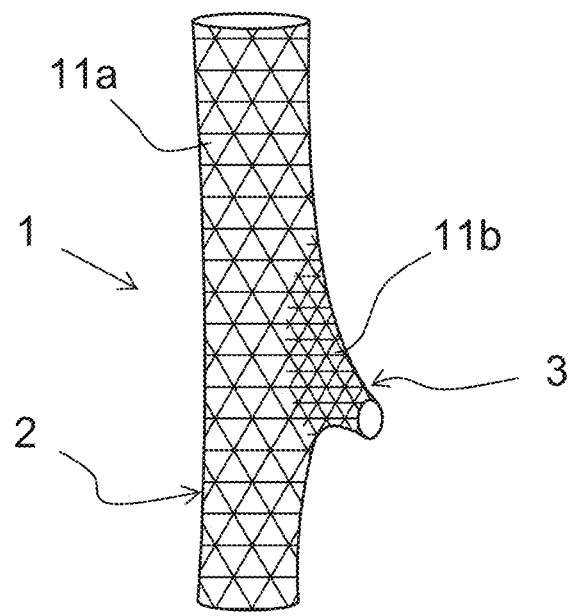
FIG. 3a shows an end view of a branched stent having a different mesh density.

FIG. 3a shows an end view of a branched stent 1 having a different mesh density. While meshes 11a having a large mesh width, i.e., a low mesh density, are indicated in the main branch 2, meshes 11b having a smaller mesh width, i.e., a high mesh density, are located in the side branch 3.

Figure 3B:
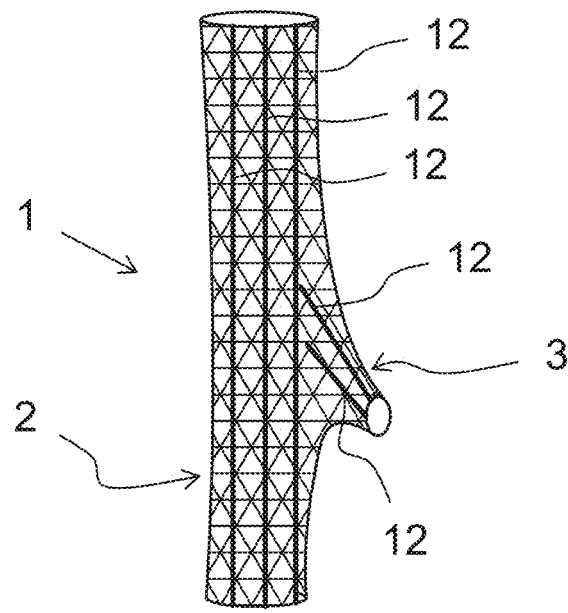
FIG. 3b shows an end view of a branched stent comprising standing threads.

In FIG. 3b, an end view of a branched stent 1 comprising standing threads 12 is represented. The standing threads 12 stiffen and reinforce the branched stent 1 in the longitudinal direction of the main branch 2 and of the side branch 3. They can also be arranged in the branched stent 1 in greater or lesser numbers than represented here, of course. The standing threads extend essentially in a straight line. In particular, it is to be noted that they do not impede the deployment of the side branch 3 into its second state.

Figure 3C:
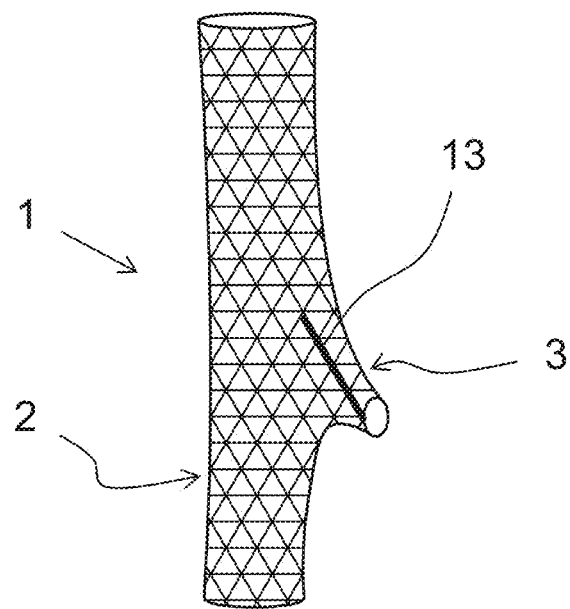
FIG. 3c shows an end view of a branched stent comprising an X-ray-visible material.

FIG. 3c shows an end view of a branched stent 1 comprising an X-ray-visible material, which is located in the side branch 3. This can be an additional thread or wire, as indicated here. An X-ray-visible coating of a portion of or the entire side branch 3 is also possible. Alternatively, one or more of the starting materials of the branched stent 1, which have been formed into meshes, can also consist of an X-ray-visible material 13. With the aid of this material 13, it is possible to position the branched stent 1 in the vessel in an optimal manner during the surgery under X-ray guidance.

Figure 3D:
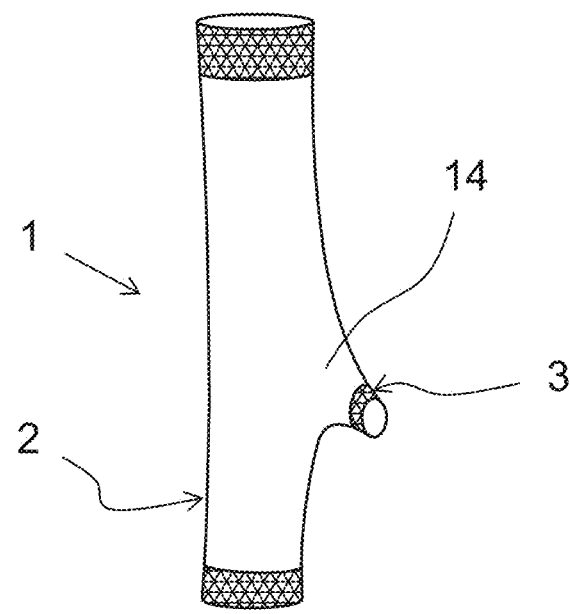
FIG. 3d shows an end view of a branched stent comprising a protective sleeve.

FIG. 3d shows an end view of a branched stent 1 comprising a protective sleeve 14. The protective sleeve 14, which is preferably impermeable for fluids, surrounds the branched stent 1, which has been produced in a textile-like manner, and therein ensures that the vessel to be supported with the aid of the branched stent 1 can be additionally sealed.

FIGS. 4a through 4i show a summary of a further exemplary embodiment of the invention in the manner of a poster. Represented therein are a branched, tubular wire mesh of the branched stent 1 as well as the deployment of a side branch 3 of the branched stent 1. In addition, the application of the invention is briefly described with reference to a particularly advantageous exemplary embodiment.

Figure 4A:
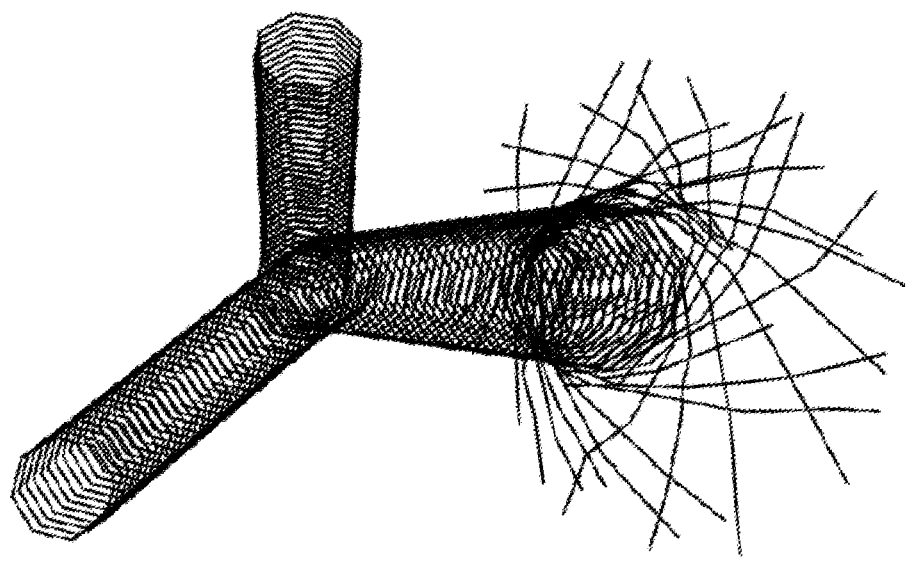
FIG. 4a shows a branched wire mesh.

FIG. 4a shows a branched wire mesh.

FIGS. 4b through 4e show a stent deployment.

FIGS. 4f through 4i show a "door opener" mode of operation, wherein FIG. 4f shows the pulling of the side branch into the main branch, FIG. 4g shows the mounting and compression of the stent onto a cardiac catheter, FIG. 4h shows the positioning of the stent, the withdrawal of the cardiac catheter, whereby the main branch deploys, and then deployment of the side branch into a bifurcation, and FIG. 4i shows the advancement and deployment of the second stent via a roll neck into the lateral branch.

Motivation and objective: Coronary stents are commercially available in highly diverse designs and are already used nowadays with great success. The uncomplicated and reliable repair of stenoses in the region of coronary bifurcations is a problem, however.

Research priorities: The superelastic nickel-titanium alloy Nitinol is selected as the material, which, in connection with the utilized braiding technology, generates the desired flexibility and simultaneously allows for an automatic, radial expansion of the stent. In the implemented concept, the transitional region to the side branch is achieved with the aid of two individual stents, wherein a stent is provided with a technique functioning as a "door opener". A Y-shaped braided tube is manufactured for the production of the stent comprising a "door opener". In the next step, the arisen side branch is drawn into the main branch similarly to a bud. Afterward, the stent is compressed, positioned in the main branch, and deployed. In the second step, the side branch, which has been retracted in the manner of a bud, deploys and the path to the lateral vessel is thereby opened and stabilized. In order to also achieve a stabilization of the lateral vessel, in the next step, a second stent having a simple tube geometry is inserted into the side branch via the "door opener".

The present invention is not limited to the represented and described exemplary embodiments. Modifications within the scope of the claims are also possible, as is any combination of the features, even if they are represented and described in different exemplary embodiments.

LIST OF REFERENCE NUMBERS 1 branched stent
2 main branch
3 side branch
4 main lumen
5 holding means
6 side branch lumen
7 side branch stent
8 stent system
9 wire
10 loop
11 mesh
12 standing thread
13 X-ray-visible material

The invention claimed is:

1. A branched stent, comprising:
a main branch having a tubular main lumen;
a side branch that branches off from the main branch;
the main branch and the side branch made from a strand-shaped starting material;
the side branch configurable between a first state in which the side branch lies within the main lumen and a second state in which the side branch lies outside the main lumen;
in the second state, the side branch defining a tubular side branch in fluid communication with the main lumen;
the side branch comprising a shape-memory material;
the main branch and the side branch formed together as a single piece textile-machined component, the single piece textile-machined component comprising one of a single braided, woven, knitted, or interknitted component of the strand-shaped starting material;
a plurality of individual and circumferentially-spaced curved loops at an end of the side branch, wherein a plurality of ends of the strand-shaped starting material in the side branch are connected to the loops such that no free ends of the strand-shaped starting material are present at the end of the side branch; and
further comprising a holding means for holding the side branch in the first state, the holding means attached to a pair of opposing loops of the plurality of individual and circumferentially-spaced curved loops at the end of the side branch.

2. The branched stent of claim 1, wherein the shape-memory material comprises a stored shaped corresponding to the second state of the side branch.

3. The branched stent of claim 1, wherein the main branch comprises a shape-memory material.

4. The branched stent of claim 1, wherein the main branch is held in a compressed state.

5. The branched stent of claim 1, wherein the main branch and the side branch are braided from the same strand-shaped starting material.

6. The branched stent of claim 5, comprising braided crossovers of the strand-shaped starting material in a region where the side branch branches off from the main branch.

7. The branched stent of claim 1, wherein the side branch branches off from the main branch at an acute angle.

8. The branched stent of claim 1, further comprising a coating applied over the main branch and the side branch.

9. The branched stent of claim 1, wherein the main branch and the side branch comprise different diameters as compared to each other.

10. The branched stent of claim 1, comprising a mesh density of the strand-shaped starting material that varies along a longitudinal axis of the main branch or varies between the main branch and the side branch.

11. The branched stent of claim 1, further comprising an X-ray-visible material in one or both of the main branch and the side branch.

12. The branched stent of claim 1, wherein at least a portion of the strand-shaped starting material comprises bioresorbable material.

13. The branched stent of claim 1, further comprising standing threads in one or both of the main branch and the side branch to stabilize the branched stent.

14. The branched stent of claim 1, further a protective sleeve around a at least a portion of one or both of the main branch and the side branch.

15. A stent system, comprising:

the branched stent according to claim 1;

a side branch stent connected to the side branch of the branched stent; and wherein a diameter of an end of the side branch stent facing the side branch is equal to a diameter of an end of the side branch facing away from the main branch.

* * * * *